United States Patent [19]
Haar et al.

[11] Patent Number: 5,977,545
[45] Date of Patent: Nov. 2, 1999

[54] SAMPLE CARRIER FOR USE IN INFRARED TRANSMISSION SPECTROSCOPY

[75] Inventors: Hans-Peter Haar, Wiesloch; Gerhard Werner, Weinheim, both of Germany

[73] Assignee: Roche diagnostics GmbH, Mannheim, Germany

[21] Appl. No.: 08/952,823
[22] PCT Filed: May 30, 1996
[86] PCT No.: PCT/EP96/02321
  § 371 Date: Dec. 3, 1997
  § 102(e) Date: Dec. 3, 1997
[87] PCT Pub. No.: WO96/39620
  PCT Pub. Date: Dec. 12, 1996

[30] Foreign Application Priority Data

Jun. 3, 1995 [DE] Germany .......................... 195 20 446

[51] Int. Cl.$^6$ .......................... G01N 21/00; G01N 21/01
[52] U.S. Cl. .............................. 250/339.12; 250/339.06; 250/458.1; 250/244
[58] Field of Search .................. 250/339.12, 339.06, 250/458.1; 356/244

[56] References Cited

U.S. PATENT DOCUMENTS

| 4,682,890 | 7/1987 | De Maracio et al. .................. 356/244 |
| 5,290,705 | 3/1994 | Davis ...................................... 436/164 |
| 5,519,218 | 5/1996 | Chang .................................. 250/339.07 |

FOREIGN PATENT DOCUMENTS

| 0 644 413A2 | 3/1995 | European Pat. Off. . |
| 40 30 699C1 | 10/1991 | Germany . |
| WO93/00580 | 1/1993 | WIPO . |
| WO95/01559 | 1/1995 | WIPO . |

OTHER PUBLICATIONS

"Optical Characterization of Diamond Synthesized Using $CH_4$–$CO_2$ gas mixtures without supplying hydrogen gas", Chen et al, Thin Solid Films 253, ElSevier, 1994, pp. 162–167.

"Carbon Dioxide Clathrates: An IR Spectroscopic Marker for Arthritis?", Eysel et al, Applied Spectroscopy, vol. 47, No. 9, 1993 pp. 1519–1521.

Primary Examiner—Constantine Hannaher
Assistant Examiner—Andrew Israel
Attorney, Agent, or Firm—Nikaido, Marmelstein, Murray & Oram LLP

[57] ABSTRACT

A sample carrier and a method for performing quantitative IR transmission spectroscopy utilizes infrared radiation of a suitable wavelength for measuring a sample. The sample carrier includes a sample platform and a holder for holding the sample platform. A thickness of the sample platform is less than one quarter of a shortest wavelength of the suitable wavelength range. The sample platform is transparent to the infrared radiation in the suitable wavelength range.

22 Claims, 7 Drawing Sheets

SAMPLE CARRIER FOR USE IN INFRARED TRANSMISSION SPECTROSCOPY

Subject matter of the invention are sample carriers for use in infrared transmission spectroscopy that have a sample zone alternatively referred to as a sample platform and a holder for holding said sample zone. Moreover, the layer thickness of the sample zone is less than one quarter of the shortest wavelength of the radiation used within the material of said zone.

Also disclosed is the application of sample carriers in quantitative infrared transmission spectroscopy, and a method and a system for performing transmission spectroscopy using said sample carriers. A further embodiment concerns sample carriers for use in IR transmission spectroscopy that have at least two sample zones on a common holder, and in which these (at least) two sample zones are made from materials that do not have any common absorbance bands with an absorbance greater than 0.1 in the infrared range used.

Sample carriers for use in infrared spectroscopy are known in the prior art that are shaped like a plane-parallel plate made from materials that are as permeable to infrared radiation as possible. German patent DE 4030699 describes such sample carriers as the prior art and proposes an improvement to said carriers in which the sample carrier is designed as a converging lens. The sample carrier materials disclosed in the prior art are potassium bromide, zinc selenide, sodium chloride and other materials that are permeable to infrared radiation. The materials used in the prior art have a thickness of many millimeters to ensure sufficient mechanical stability.

Also known from the prior art are infrared sample carriers from 3M called "disposable IR cards". These sample carriers consist of a cardboard strip with an opening. The opening in the cardboard is closed with a sample zone made from either polyethylene or PTFE (poly-tetrafluoroethylene). The 3M sample carriers have the disadvantage that the absorption bands of polyethylene and PTFE may overlap the absorptions of the sample material to be tested. In particular, each of the materials used in the sample zone has relatively strong bands that usually cannot be eliminated, even using differential measurement. Such sample carriers can therefore usually not be used to perform quantitative analysis.

The object of the present invention was to propose easy-to-use sample carriers that, due to their characteristics in the infrared range, make it possible to perform quantitative infrared spectroscopy. The object is solved by the sample carriers according to the invention that have a holder to hold a sample zone, and a sample zone with a layer thickness less than one quarter of the shortest wavelength of the radiation used within the sample material. In developing suitable sample carriers, the first attempt was to improve the sample carriers known in the prior art by decreasing the layer thickness. Experiments using sample carriers with a layer thickness in the range of 20 μm did not yield convincing results. It was not possible to quantitatively reproduce spectra that were absorbed by semiconductive materials with this layer thickness. It was shown that interference phenomena appear that strongly depend on the thickness of the material, so that even relatively small deviations in the thickness of the sample zone due to manufacture lead to fluctuations in intensity. Moreover, wavelength-dependent fluctuations in intensity appear in thicknesses of many micrometers that overlap the spectrum of the sample, making it very difficult or impossible to perform a quantitative evaluation. Surprisingly, quantitatively reproducible spectra can only be absorbed in an area that is less than 1000 nm thick. It has been shown that the sample zone should have a layer thickness that is less than one quarter of the wavelength of the shortest measurement wavelength within the material of said zone. The upper limit of thickness for the sample zone depends on the material from which it is made, due to the known fact that the wavelength depends on the refractive index of the material in which the wavelength propagates. An advantage of sample carriers according to the invention is that the absorption in the sample zone is minimal, and the sample spectra are therefore only negligibly affected. Interference phenomena are also avoided with sample carriers according to the invention. Moreover, the sample carriers are easy to use as compared with the KBr molding method or the method using NaCl plates. Sample carriers according to the invention also have the advantage of low manufacturing costs, which makes them suitable for disposable use. Carryover and contamination problems are also eliminated with disposable sample carriers.

Infrared spectrometers for performing IR transmission measurements are sufficiently known in the prior art. The Fourier IFS 25 transform spectrometer from Bruker, for instance, is suitable for performing measurements with sample carriers according to the invention. The sample carriers according to the invention can be used in either Fourier transform or dispersion spectrometers. To do so, they are placed in a holder on the infrared spectrometer and exposed to infrared radiation.

In an initial embodiment of a sample carrier according to the invention, the sample carrier has a holder and a sample zone with a thickness that is less than one quarter of the shortest measurement wavelength within the material of the sample zone. The sample carrier can also have numerous sample zones for performing numerous assays.

The holder of the sample carrier is usually shaped like a thin plate that is manufactured from a material having the appropriate stiffness. Suitable materials are, for instance, plastics, cardboards, metals and glass. The holder contains one or more openings in which or on the edges of which the sample zone is attached. Moreover, the holder has an area that is used for the manual or automatic handling of the sample carrier. In addition, the holder can have elements such as notches, recesses, projections or the like for positioning the sample carrier in the infrared spectrometer. Suitable devices such as rack, roughed areas and the like can be provided to facilitate transport of the sample carrier into the infrared spectrometer.

The sample zone is attached to the holder or in the recess of the holder in such a way that the recess in the holder is closed by the sample zone. The sample zone is shaped like a thin plate or film made from a material that is permeable to infrared radiation. Suitable, preferred materials are silicon, germanium and diamond. In general, materials have proven to be advantageous that have an absorption in the infrared range that is continous and as minimal as possible. Many semiconductive materials are particular suitable for such materias. The oncept of a semiconductive material in this sense is understood to include not only individual chemical elements, but composed semiconductors as well, such as binary and ternary semiconductors. It has also proven advantageous when the semiconductive materials have a large band gap and no contaminations or dopings. Given the extremely small layer thicknesses of the sample zone according to the invention, materials can also be used that have absorption bands in the infrared range, the absorbance (absorptivity) of which cannot be too high, however.

According to the invention, therefore, plastic films made from polyesters, polystyrenes, polyethylenes, polypropylenes, etc. are suitable. A polyester called Mylar® from DuPont has proven to be especially suitable for the application according to the invention. Very thin and consistently thick plastic films can be achieved in manufacture using a stretching process, for instance.

The thickness of the sample zone is preferably less than 1000 nm or, even better, less than 500 nm. Experiments have shown that the thickness of the sample zone must be less than one quarter of the shortest wavelength used for measuring in order to achieve qua ntitatively reproducible spectra. The range of the middle infrared light is between 2.5 and 25 $\mu$M (4000–400 cm$^{-1}$). The sample zone to be measured in this infrared range should therefore have a layer thickness of less than 500 nm. The infrared range 7–13 $\mu$m is particularly interesting for the detection and quantitative determination of many analytes, however. Sample zones with a layer thickness of less than 2 $\mu$m, and especially less than 1 $\mu$m are therefore suitable for this range.

Due to the extremely thin nature of the materials used in the sample zone, the size of the opening(s) in the holder of the sample carrier should not be too large, to ensure sufficient stability of the sample zone. Each of the openings in the holder should have a cross-section that is less than 10 mm, and preferably less than 5 mm. To ensure the stability of the sample zone, it has proven advantageous for the openings in the holder to be circular.

The sample zone can be attached to the holder by glueing, melting or pressing it on the holder. It has been shown that, in many cases, adhesion is sufficient to hold thin films in place on the holder. The film can be attached to the holder in such a way that it lies on the holder and covers the recess. In another embodiment, the sample zone is attached inside the holder recess. Moreover, one-piece embodiments of the sample carriers are well-suited; they can be made from plastics using injection molding, for instance.

Like the 3M sample carriers, sample carriers according to the invention are also possible in which the holder has two layers with at least one opening each and the sample zone in between. The sample zone is held between the layers by means of glueing, pressing, etc. in such a way that it can be accessed through the openings in the layers.

When semiconductive materials are used for the sample zone, the methods discussed above can be used to bond the holder and sample zone together. In addition, however, a manufacturing method is possible in which a plate made from a semiconductive material is subjected to an etching process so that the thickness of the plate is reduced to less than 1000 nm in an area that forms the sample zone after the etching. This process produces a one-piece embodiment of the sample carrier. It is also advantageous to subject a semiconductive plate with a relatively small thickness to the same etching process in order to produce a plate that has a zone with a thickness of less than 1000 nm. As an advantage, the plate that is produced in this process can be placed on a holder. Using this procedure it is possible to manufacture a carrier according to the invention using a relatively small quantity of semiconductive material. With regard for the manufacture of sample carriers from semiconductive materials, reference is made to all points of the processes described in WO 95/01559 (pages 6 and 7).

As an alternative, it is also possible to create the sample zone with a thickness of less than 1000 nm needed for the invention by means of sputtering, chemical vapor deposition (CVD) or molecular beam epitaxy.

With regard for the manufacture of a film made from diamond, reference is made to all points of the article "Optical characterization of diamond synthesized using $CH_4$—$CO_2$ gas mixtures without supplying hydrogen gas" in Thin Solid Films 253 (1994), pages 162–167. The following process is mentioned as an example of a sputtering process:

A plastic layer that is a few millimeters thick is applied to a thin glass plate. In a subsequent step, a recess with a cross-section of a few millimeters is cut out of the plastic layer. The opening in the plastic layer is filled with a silicon layer less than 1000 nm thick by means of a sputtering process, so that the opening is completely closed. In a final manufacturing step, the glass plate—which was used as the carrier—is removed in an etching process using hydrofluoric acid.

In a second embodiment of the sample carriers according to the invention, said sample carriers have at least two sample zones that are attached to a common holder. In this embodiment, the thickness of the sample zones is much less critical than in the first embodiment described above. Sample zones in the range of from many micrometers up to one millimeter are possible. An essential element of the second embodiment of sample carriers is that the minimum of 2 sample zones consist of materials that do not have any common absorption bands with an absorbance greater than 0.1 in the infrared range 7–13 $\mu$m. Suitable combinations of materials for sample zones that meet these conditions are polyethylene and PTFE, silicon and germanium, for instance.

In general, suitable combinations of plastics can be found in which an initial plastic is selected that has a few, sharply defined absorbance bands (e.g. polyester, polyvinylchloride, polymethylmethacrylate, polyethylene and polystyrene). The second plastic in the combination is a plastic that is similar to the first plastic in terms of constitution, but its hydrogen atoms are replaced with deuterium.

In the second embodiment of sample carriers, at least two spectra are absorbed for the same sample fluid. Due to the condition required according to the invention, i.e. that the materials in the sample zone not have any common absorption bands, the information provided from the minimum of two absorbed spectra can be combined in such a way that the spectra of the sample material in the infrared range used are not covered by the absorption bands of the sample zones. It has been shown that the conditions for absorbance of a quantitative transmission spectrum are given when the absorption bands of the sample zones in the infrared range 7–13 $\mu$m have an absorbance that is less than 1, and preferably less than 0.3. The terms absorbance and absorptivity are used interchangeably. They are defined by the decadic logarithm of the quotient of incident intensity and intensity that has passed through.

The second embodiment of sample carriers can be designed in such a way that the holder has at least two separate recesses that contain sample zones. At least two different types of materials having the characteristics described above are selected for the sample zones. If the criterium required for the invention, i.e. that none of the absorption bands overlap, cannot be met with two materials, additional sample zones made from additional materials can be used.

In a preferred embodiment of the invention, a film (and a plate, if necessary) is selected for the sample zones in which at least two different materials abut each other. Sample zones of this nature can be made in particular from plastics in a suitable fashion by melting together two strips of different plastics.

Sample carriers according to the first and second embodiments are preferably manufactured as products for one-time use.

Two measurements are performed to investigate a sample using sample carriers according to the second embodiment. For this purpose, small quantities of the same sample are applied to at least two sample zones. After this, an infrared spectrum is absorbed by each of the two sample zones. The two infrared spectra that are obtained are combined using an evaluating unit such as a computer in such a way that one spectrum of the sample material is obtained that is not overlapped by absorption bands from materials within the sample zones. The decision as to which wavelength ranges of the measurements to use after they have been performed can be made by determining the spectra of the sample zones before applying sample to the sample zones. The ranges in which absorption bands from materials in the sample zones are present are stored in the evaluating unit. These ranges are not taken into consideration later when a combination spectrum is created from the spectra recorded individually. If ranges are present in which neither sample zone has any absorption bands, these ranges can be used to match the spectra with each other, i.e. to perform baseline corrections and define a scale of the spectra obtained. Moreover, these ranges are advantageous for determining the relative quantities of sample on the two materials of the sample zones. This is especially important when the sample is applied with a single pipetting step to the zone in which both of the adjacent materials of the sample zone are wetted with sample.

The sample carriers according to the invention can also be used to create qualitative infrared spectra, but they are especially advantageous for use in quantitative infrared spectroscopy. To perform quantitative infrared spectroscopy to determine the concentration of an analyte in the sample, it is necessary that defined quantities of sample be applied to the sample zones. When using a sample carrier according to the second embodiment, it is preferable for the same quantity of sample material be applied to the minimum of two sample zones. Duplicate sample application can be avoided by using a sample carrier in which the minimum of two sample zones are situated directly next to each other. In this case, the sample is preferably applied in such a way that the same quantities of sample enter each of the two zones of the sample zone. If this cannot be ensured, spectral ranges that are measured with the two zones can be used in order to determine the quantity distributed between the zones.

In addition to the embodiment of the method described above for infrared spectroscopy in which blank spectra of the sample zones are recorded, it is also possible to store the information on the materials of the sample zones in the evaluating unit, or to read them in, preferably directly from a bar code on the sample carrier. In this case, the evaluating unit can select each of the ranges that are used in the evaluation without recording blank spectra.

The spectra of the sample zones without sample can be used to determine the actual characteristics, i.e. especially the thickness, of the sample zone, because these parameters can fluctuate depending on manufacture. When the material in the sample zone is known, the absorption bands can be used to deduce the thickness of the sample zone. These data can be used to correct the sample spectra, e.g. to take the absorption of the sample zones into account and if necessary, substract them from the spectra obtained with sample.

A method for performing quantitative transmission spectroscopy using sample carriers according to the first or second embodiment is described below.

A defined quantity of sample is applied to the sample zone of the sample carrier. The term sample is especially understood to be liquids within the context of this invention. Clinically relevant sample fluids can include blood, serum, hemolysate, urine, saliva, tears, etc. However, the invention can also be used for sample fluids obtained from a liquid chromatograph, for instance. The sample quantities can be applied using means known in the state of the art, e.g. micropipettes. To perform a spectroscopy using sample carriers according to the invention sample quantities in the range of a few microliters are usually used.

To perform a measurement, the sample carrier is placed in an infrared spectrometer, using the holder to position it so that the sample is detected by the infrared beam of the instrument. The infrared spectrometer can also be equipped with a bar code reader, a magnetic strip reader or another type of data acquisition device that enters data on the sample carrier and, if necessary, information for spectral analysis.

For the case in which the sample carrier has numerous sample zones, e.g. for evaluating a number of different samples, or if a sample carrier according to the second embodiment is used, it is advantageous for the infrared spectrometer to also be equipped with a transport device that makes it possible to position the sample carrier in the spectrometer in such a way that the space-fixed measuring beam detects each of the sample zones in succession.

If a sample zone is located in the region of the measuring beam, it is detected by infrared radiation. Preferably, the measurement is performed in such a way that the entire sample is measured integrally, i.e. the entire quantity of sample is located within the measuring beam. In this case, a quantitative measurement can also be performed if the sample is not distributed evenly on the sample zone.

The quantity of one or more analytes in the sample is determined based on the transmission spectrum of the sample. The quantitative evaluation of infrared spectra belongs to the state of the art and will therefore not be explained in any greater detail here. Reference is made to the literature cite "Applied Spectroscopy, Vol. 47, pages 1519 to 1521 (1993)" with regard for procedures for evaluating spectra, and to patent application EP-A-0 644 413 with regard for performing quantitative spectroscopy.

Analytes within the context of this invention are understood to be all substances that absorb radiation in the infrared range and that can be characterized based on this radiation. This is meant to include, in particular, analytes that are interesting for clinical chemistry, such as glucose, proteins, hormones, glycerides, lipids, enzymes, pharmaceuticals, drugs, etc.

To perform a quantitative IR transmission spectroscopy, it has proven to be advantageous to dry liquid samples before performing the spectroscopy.

The sample carriers according to the invention are explained in greater detail using the following figures:

FIG. 1a shows a sample carrier according to the invention in three dimensions. The sample carrier has a holder (1) with an opening (2) having a diameter of 5 mm The holder (1) also has a recess (3) that serves to position the sample carrier by means of a light barrier. The holder also has ridges (4) that makes it easier to handle, and a bar code (5) the contains information on the sample carrier. This information can concern the material of the sample zone or its thickness, for instance.

Figures 1, 1A:
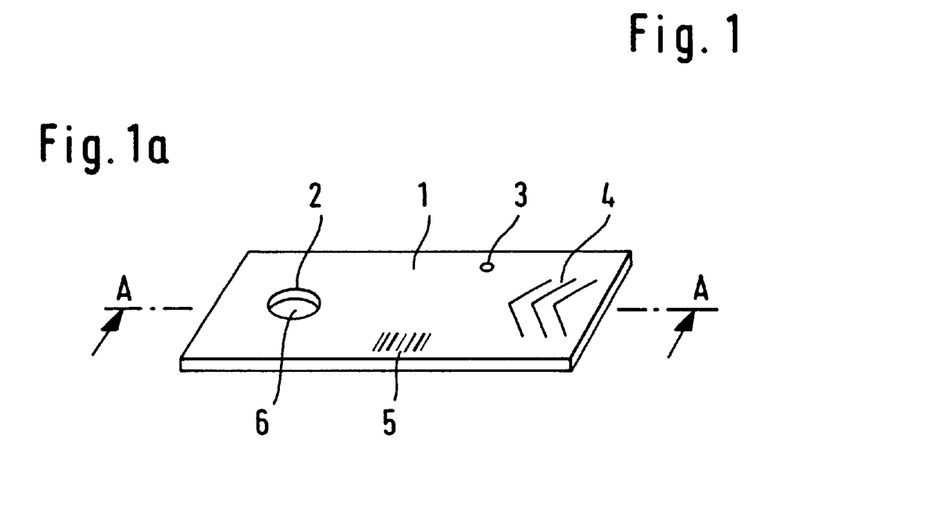
Figure 1B:
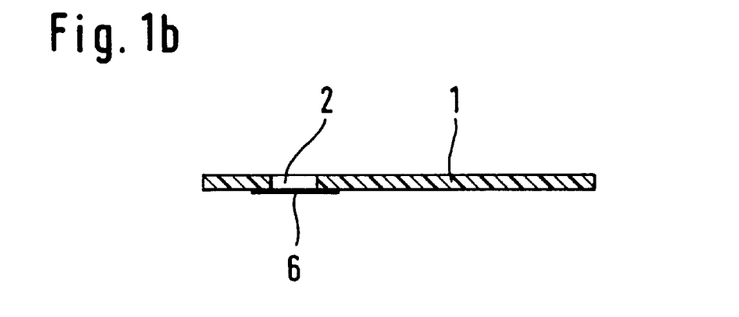
FIG. 1: Sample carrier with a sample zone

FIG. 1b shows the sample carrier depicted in FIG. 1a along the line A—A. The opening (2) in the holder (1) is closed by the sample zone (6). In the case shown, the holder comprises a polystyrene plate that is 2 mm thick, 5 cm long, and 2 cm wide. The opening (2) is circular and has a cross-section of 5 mm. A 400 nm-thick piece of film made from Mylar® was used as the sample zone. The holder (1) and the sample zone (6) were bonded to each other by means of ultrasonic welding.

Figure 1C:
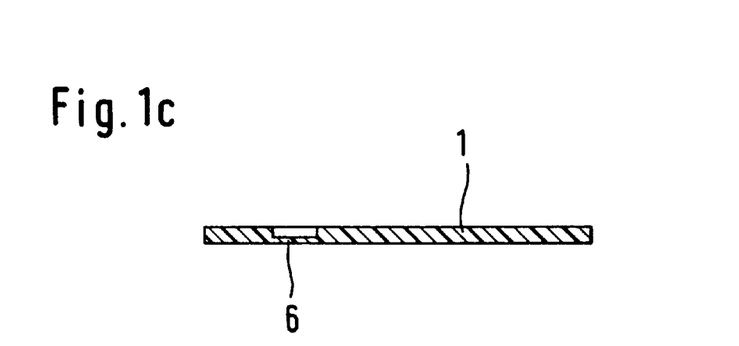

FIG. 1c shows a cross-section of a one-piece embodiment of a sample carrier according to the invention. The sample carrier has a holder (1) made from polymethyl methacrylate that has a sample zone that is 500 nm thick. The sample carrier can be made using an injection molding process.

Figures 2, 2A:
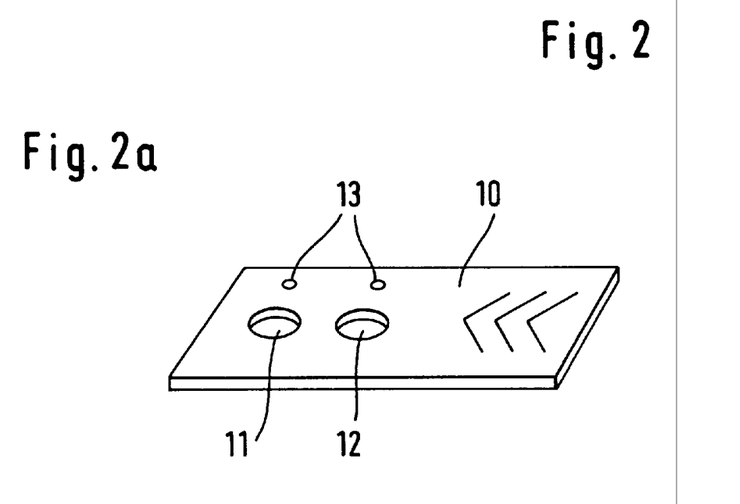
FIG. 2: Sample carrier with two sample zones made from different materials

FIG. 2a shows a sample carrier with a holder (10) in which two openings are provided as sample zones. The openings are circular and have a thin cross-section of 5 mm. The first opening is closed by means of a sample zone (11) made from polyethylene, while the second opening is closed by means of a second sample zone (12) made from deuterized polyethylene. In addition to the openings in the holder mentioned above, smaller openings (13) are present that serve to position the sample carrier in the spectrometer by means of light barriers.

Figure 2B:
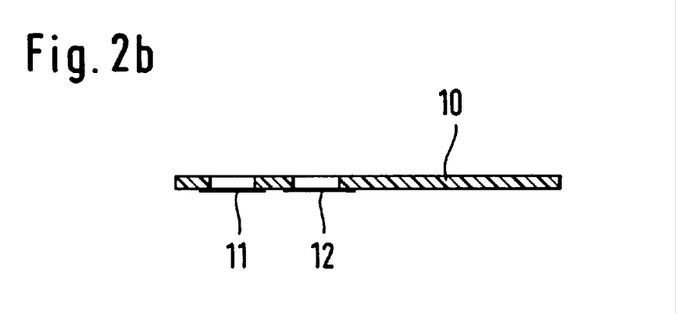

FIG. 2b shows a cross-section of the sample carrier shown in FIG. 2a.

Figure 2C:
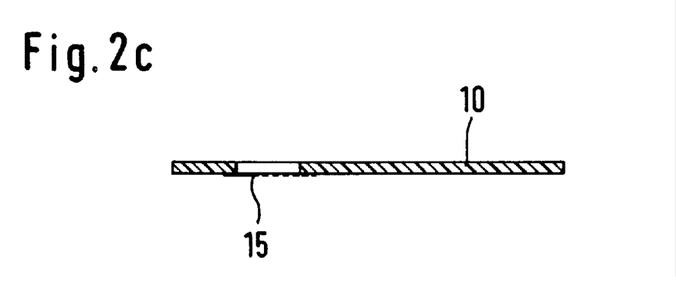

FIG. 2c shows a cross-section of a sample carrier in which a plastic film that consists of two plastics that abut each other is placed in one opening.

Figure 3:
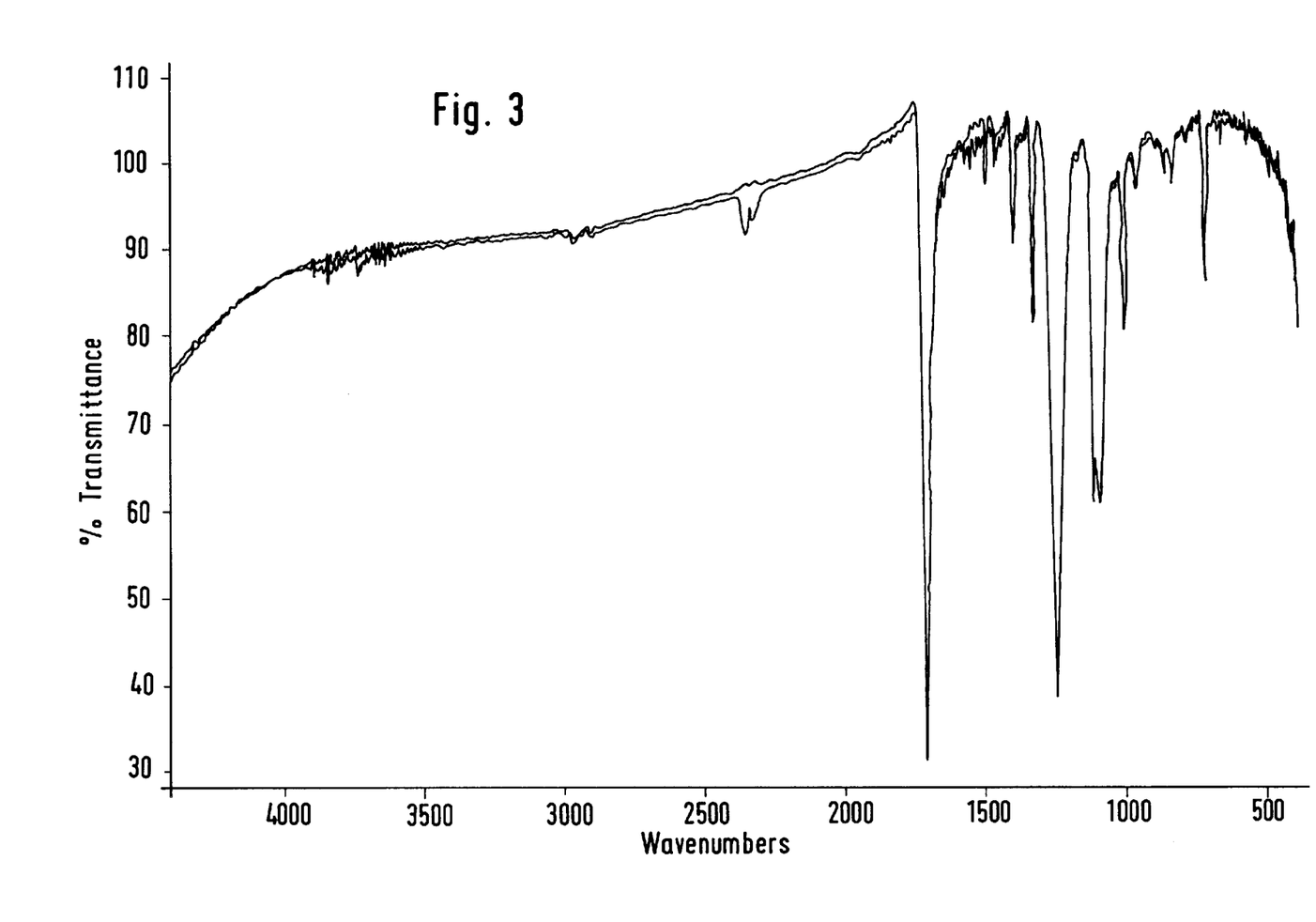
FIG. 3: IR transmission spectrum of a Mylar® film

FIG. 3 shows a transmission spectrum of a 400 nm Mylar® film. The spectrum shows that the plastic is especially well suited for use as a carrier material, because it exhibits virtually no absorption bands at wavelengths above 1800 cm$^{-1}$ and up to 4000 cm$^{-1}$.

Figure 4:
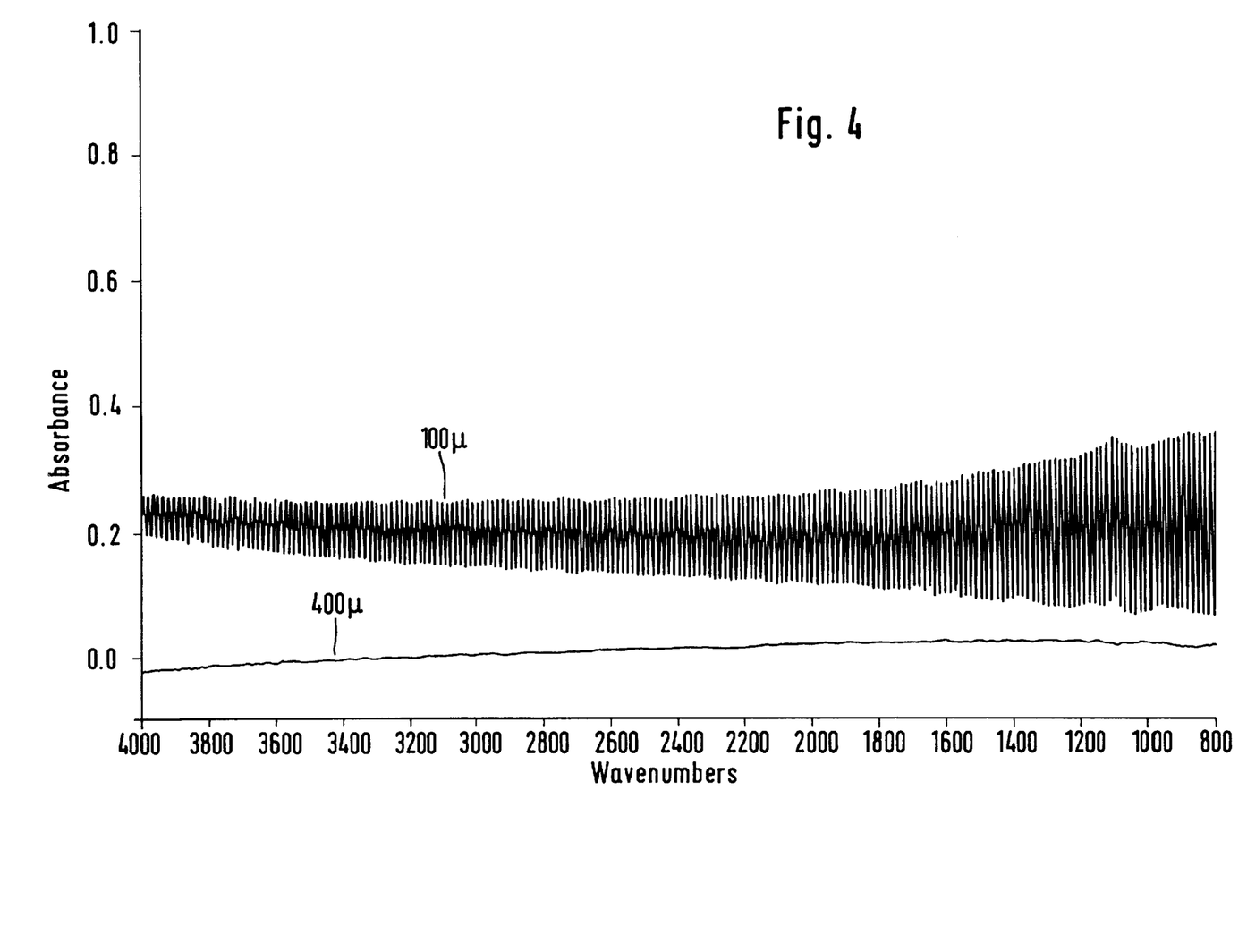
FIG. 4: IR transmission spectra of silicon films

FIG. 4 shows transmission spectra of silicon films having different thicknesses. To record these spectra, the spectrometer was calibrated so that no absorption is displayed for a silicon film that is 400 $\mu$m thick. A silicon film of this thickness has a radiation absorption of about 50%. The curve shows, however, that the absorption of a 400 nm silicon film is very even across the entire spectral region measured and has no bands or oscillations. The upper curve that was obtained based on a measurement of a 100 $\mu$m silicon film, on the other hand, exhibits strong oscillations. Even minimal changes in the thickness of the film cause the oscillations to shift in position. This means that silicon film with a thickness of 100 $\mu$m cannot be used in infrared spectroscopy.

Figure 5:
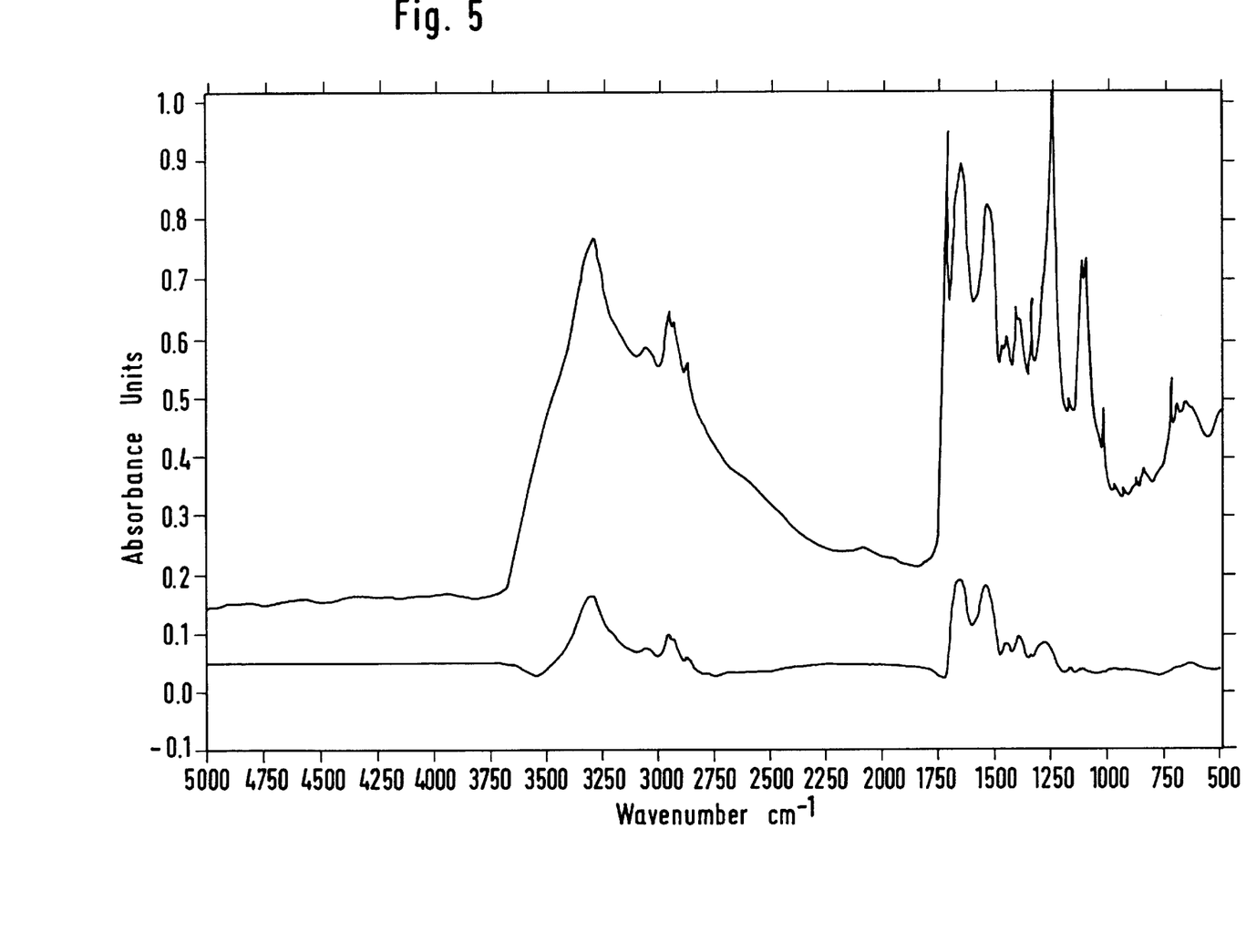
FIG. 5: IR transmission spectrum of BSA (bovine serum albumin) in physiological saline solution

FIG. 5 shows the spectrum of bovine serum album in (BSA) in a physiological saline solution. The absorbance is plotted on the ordinates and the wavelengths are plotted on the abscissa. The measurement was performed on a 400 nm Mylar® film. The curve below it shows the standard deviation curve of the spectrum that was determined with 13 individual measurements.

Figure 6:
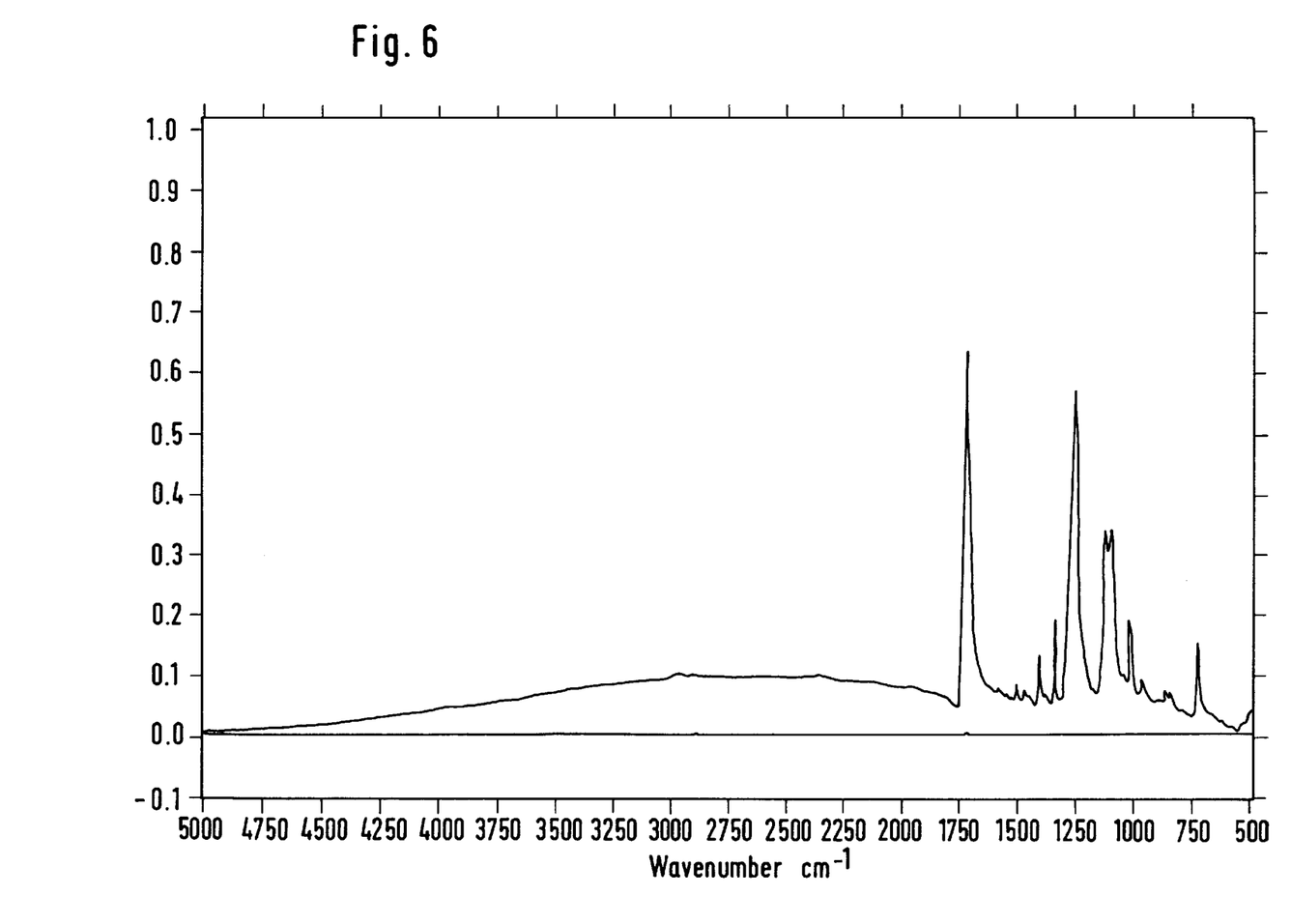
FIG. 6: IR transmission spectrum of a 400 nm Mylar® film

FIG. 6 shows an IR transmission spectrum of a 400 nm Mylar® film without sample. The curve below it represents a standard deviation spectrum from 13 individual measurements. From this standard deviation spectrum it can be seen that the oscillation of absorbance shown in FIG. 4 is not present for sample carriers that are 100 nm thick.

Figure 7:
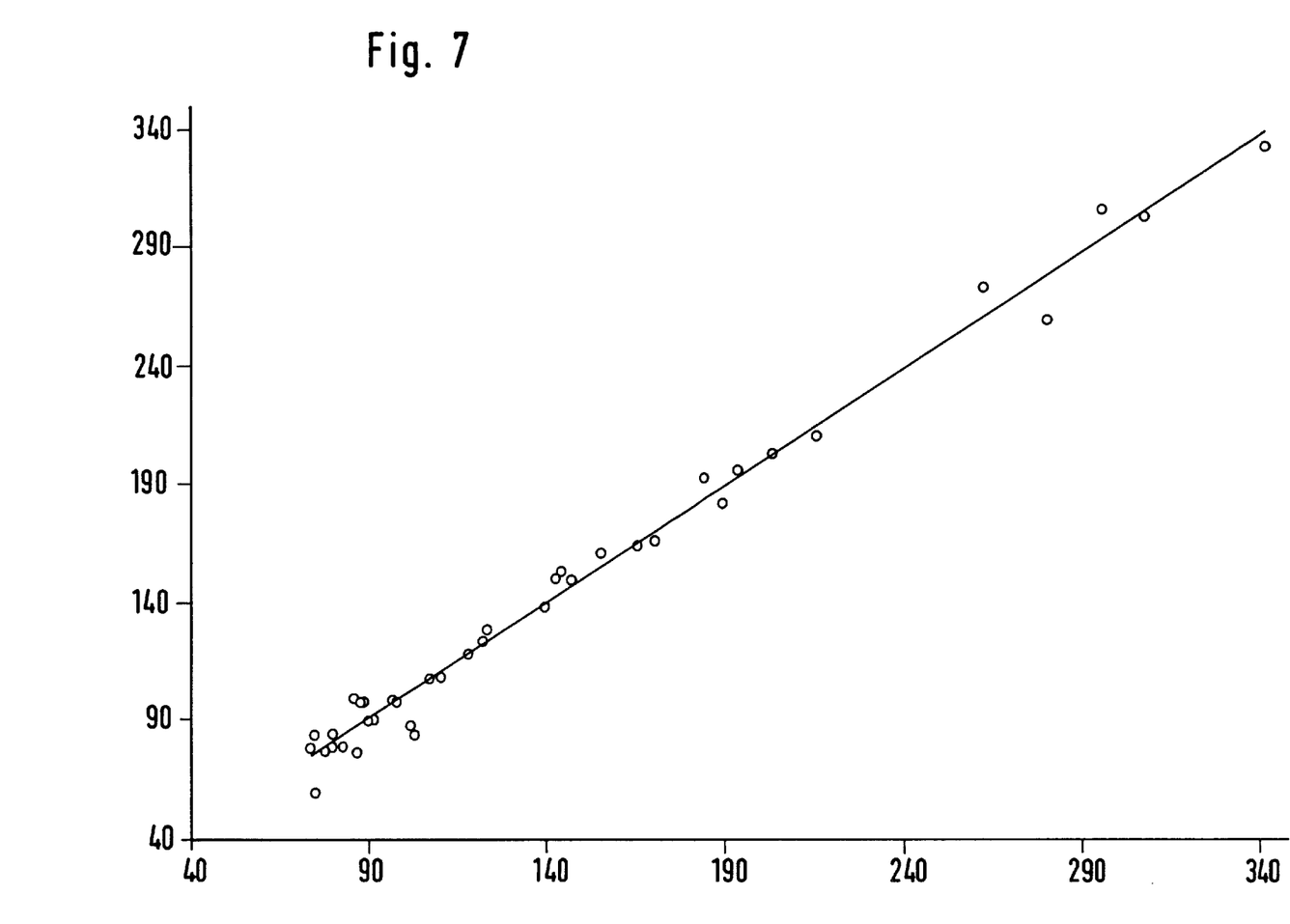
FIG. 7: Quantitative glucose determination on a 400 nm Mylar® film

FIG. 7 shows the results of a quantitative determination of glucose in water using infrared spectroscopy on a 400 nm Mylar® film. The sample weight of glucose is plotted on the abscissa in mg/dl water, while the value obtained using infrared spectroscopy is plotted on the ordinates. The infrared spectroscopy was carried out in the range 975–1200 cm$^{-1}$, and the concentration was determined in this range based on the absorbance. The position of the points plotted around the angle bisector in FIG. 7 shows that a quantitative glucose determination can be performed using sample carriers according to the invention.

We claim:

1. A sample carrier for use in infrared transmission spectroscopy using infrared radiation of a suitable wavelength range for measuring a sample, comprising a sample platform, and a holder for holding the sample platform, wherein a thickness of the sample platform is less than one quarter of a shortest wavelength of the suitable wavelength range, said sample platform being transparent to the infrared radiation in the suitable wavelength range.

2. A sample carrier according to claim 1, wherein the thickness of the sample platform is less than 1000 nm.

3. A sample carrier according to claim 2, wherein the platform thickness is less than 500 nm.

4. A sample carrier according to claim 3, wherein the platform thickness is less than 200 nm.

5. A sample carrier according to claim 1, wherein the sample platform is a silicon, germanium, zinc selenide or diamond platform.

6. A sample carrier according to claim 5, wherein the sample platform and the sample holder are of the same material, and wherein the sample platform comprises a portion of the sample holder etched to a thickness of less than 1000 nm.

7. A sample carrier according to claim 1, wherein the sample platform is a plastic film.

8. A sample carrier according to claim 7, wherein the plastic is a polyester.

9. A sample carrier according to claim 7, wherein the plastic film is made from a combination of plastics.

10. A sample carrier according to claim 1, wherein the sample carrier comprises a plurality of sample platforms.

11. A sample carrier according to claim 1, wherein the sample carrier is suitable for use in quantitative infrared transmission spectroscopy.

12. A sample carrier for IR transmission spectroscopy comprising at least two sample platforms, and a common holder for holding the sample platforms, wherein, in the infrared range of 7–13 $\mu$m the at least two sample platforms are made from materials having absorption bands which do not overlap where both absorption bands have an absorbance greater than 0.1.

13. A sample carrier according to claim 12, wherein the absorption bands of the sample platforms have an absorbance of less than 1 in the infrared range 7–13 $\mu$m.

14. A sample carrier according to claim 12, wherein the sample carrier has first and second sample platforms made from plastic, wherein the first platform is made from a first plastic selected from the group comprising polyester, polyvinyl chloride, polymethylmethacrylate, polyethylene, polypropylene and polystyrene, and the second platform is made from a second plastic the same as the first plastic in terms of constitution, but the hydrogen atoms of the second plastic are substituted by deuterium.

15. A sample carrier according to claim 12, wherein at least two sample platforms directly abut each other.

16. A sample carrier according to claim 12, wherein the holder has at least one opening and a sample platform is attached to the edge of the at least one opening.

17. A sample carrier according to claim 16, wherein the sample platform is attached to the edge of the at least one opening by means of adhesion, glueing, melting or pressing.

18. A sample carrier according to claim 1, wherein the holder comprises two layers, disposed one on top of the other, wherein each layer comprises an opening, and wherein the sample platform is disposed between the layers at a location such that the platform is accessible through the openings in the layers.

19. A sample carrier according to claim 12, wherein the sample carrier is suitable for use in quantitative infrared transmission spectroscopy.

20. A method for performing quantitative IR transmission spectroscopy comprising the steps of:
  a) applying a defined quantity of a sample to a sample platform of a sample carrier, said sample platform being provided with a thickness of less than one quarter of a shortest wavelength of a suitable wavelength range of infrared radiation;
  b) exposing the sample to a bundle of infrared radiation in the suitable wavelength range directed essentially vertically to the sample zone;
  c) detecting radiation transmitted through the sample and the sample platform; and
  d) calculating the quantity of one or more analytes present in the sample based on a measurement of the transmitted radiation and the defined quantity of sample applied to the sample zone.

21. A method according to claim 20, wherein the sample is a liquid and the sample is dried before an infrared spectrum is measured.

22. A system for performing a quantitative infrared transmission spectroscopy measurement comprising:
  a) an infrared spectrometer including an evaluating unit; and
  b) a sample carrier comprising at least one sample platform and a holder for the at least one sample platform, wherein the sample platform has a thickness which is less than one quarter of a shortest wavelength of radiation used for the measurement.

* * * * *